United States Patent
Marentis et al.

(10) Patent No.: US 10,357,183 B2
(45) Date of Patent: Jul. 23, 2019

(54) RETAINED OBJECT TAG AND DETECTION METHOD

(71) Applicant: The Regents of the University of Michigan, Ann Arbor, MI (US)

(72) Inventors: Theodore Marentis, Ann Arbor, MI (US); Nikolaos Chronis, Ann Arbor, MI (US); Anurag Tripathi, Chandler, AZ (US); Heang-Ping Chan, Ann Arbor, MI (US); Lubomir Hadjiyski, Ann Arbor, MI (US); Amrita Ray Chaudhury, Ann Arbor, MI (US); Lucas James Rondon, South Lyon, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1130 days.

(21) Appl. No.: 14/376,203

(22) PCT Filed: Feb. 4, 2013

(86) PCT No.: PCT/US2013/024671
§ 371 (c)(1),
(2) Date: Aug. 1, 2014

(87) PCT Pub. No.: WO2013/116862
PCT Pub. Date: Aug. 8, 2013

(65) Prior Publication Data
US 2015/0018671 A1    Jan. 15, 2015

Related U.S. Application Data

(60) Provisional application No. 61/594,827, filed on Feb. 3, 2012.

(51) Int. Cl.
*A61B 5/00* (2006.01)
*A61B 5/06* (2006.01)
(Continued)

(52) U.S. Cl.
CPC ............... *A61B 5/06* (2013.01); *A61B 6/12* (2013.01); *A61B 90/39* (2016.02); *A61B 6/508* (2013.01);
(Continued)

(58) Field of Classification Search
CPC ........... A61B 19/54; A61B 90/39; A61B 5/06; A61B 6/12; A61B 2090/3966; A61B 2090/3983; A61B 2090/3995; A61B 6/508
See application file for complete search history.

(56) References Cited

U.S. PATENT DOCUMENTS 5,664,582 A    9/1997  Szymaitis
7,465,847 B2   12/2008 Fabian
(Continued)

OTHER PUBLICATIONS

International Search Report for PCT/US2013/024671, dated May 15, 2013, 4 pages.
(Continued)

*Primary Examiner* — Joel Lamprecht
(74) *Attorney, Agent, or Firm* — Reising Ethington P.C.

(57) ABSTRACT

A retained object tag, and a method of detecting the presence of a retained object or the retained object tag in a medical image. The method can include different steps such as identifying one or more potential sites in the medical image where the retained object or retained object tag may be present. The method can also include analyzing one or more features of the identified potential site against one or more predetermined properties of the retained object or the retained object tag. And the method can include determining whether the identified potential site is a retained object or a retained object tag based in part or more upon the analyzed feature.

32 Claims, 8 Drawing Sheets

(51) Int. Cl.
    *A61B 6/12*     (2006.01)
    *A61B 90/00*    (2016.01)
    *A61B 6/00*     (2006.01)

(52) U.S. Cl.
    CPC .............. *A61B 2090/3966* (2016.02); *A61B 2090/3983* (2016.02); *A61B 2090/3995* (2016.02)

(56) References Cited

U.S. PATENT DOCUMENTS

| | | | |
|---|---|---|---|
| 9,757,076 B2 * | 9/2017 | Schoonenberg | A61B 5/0084 |
| 2003/0066537 A1 | 4/2003 | Fabian et al. | |
| 2005/0016776 A1 | 1/2005 | Ballard | |
| 2009/0076382 A1 | 3/2009 | Shepherd et al. | |
| 2011/0071623 A1 * | 3/2011 | Finch | A61B 17/0057 |
| | | | 623/2.11 |
| 2011/0098553 A1 * | 4/2011 | Robbins | A61B 5/055 |
| | | | 600/410 |
| 2012/0201421 A1 * | 8/2012 | Hartmann | A61B 6/12 |
| | | | 382/103 |

OTHER PUBLICATIONS

Written Opinion for for PCT/US2013/024671, dated May 15, 2013, 5 pages.

* cited by examiner

RETAINED OBJECT TAG AND DETECTION METHOD

CROSS-REFERENCE TO RELATED APPLICATION

This application claims the benefit of U.S. Provisional Patent Application No. 61/594,827 filed Feb. 3, 2012, the entire contents of which are hereby incorporated by reference.

TECHNICAL FIELD

This invention relates to ways of detecting the presence of retained objects located inside of a patient's body during or after a surgical procedure, and relates to retained object tags.

BACKGROUND OF THE INVENTION

Gossypiboma is the term often used to describe objects like sponges, gauzes, and towels unintentionally left inside of a patient's body after a surgical procedure is completed. Other objects that can be unintentionally left inside of a patient's body include surgical implements, operating instruments, surgical needles, and tools. If left behind, the objects can lead to morbidity, mortality, and other post-surgery complications. One attempt to keep track of objects in an operating room is a practice commonly referred to as "the surgical count" in which a nurse tallies the number of objects handed to a surgeon, and ensures the same number is handed back. Other attempts involve applying bar-code and radio-frequency identification (RFID) technologies to the objects so that the objects can be accounted for and possibly located following their use. Still other technologies involve the attachment of radiopaque markers such as those disclosed in U.S. Pat. No. 7,465,847. While the surgical count and the technologies have helped to some extent, shortcomings remain such as the addition of operating room or post-surgery steps, false positives, false negatives, inaccuracies, and imprecisions.

SUMMARY OF THE INVENTION

According to one aspect, there is provided a retained object tag that may include a body, a first marker, a second marker, and a third marker. The body is attachable to an object and is made at least partly of a radiolucent material. The first marker is carried by the body and is made at least partly of a radiopaque material. The second marker is carried by the body and is made at least partly of a radiopaque material. And the third marker is carried by the body and is made at least partly of a radiopaque material. The first, second, and third markers are located in the body at positions with respect to one another that provides a space between two or more of the markers. In this way, when the retained object tag is imaged in a medical image at different orientations, the space facilitates manual and computer aided detection of the retained object tag.

According to another aspect, there is provided a method of detecting the presence of a retained object in a medical image. The method may include several steps. One step includes receiving the medical image. Another step includes identifying one or more potential sites in the medical image in which the retained object may be present. Another step includes analyzing one or more features of the identified potential sites against one or more pre-determined properties of the retained object. Yet another step includes determining whether the identified potential sites are the retained object based in part or more upon the analyzed features. And another step includes outputting the determination.

BRIEF DESCRIPTION OF THE DRAWINGS

Preferred exemplary embodiments of the invention will hereinafter be described in conjunction with the appended drawings, wherein like designations denote like elements, and wherein:

FIGS. 8A-8C shows the retained object tag of FIG. 6 at different orientations, where FIG. 8A shows a top or flat orientation.

DETAILED DESCRIPTION OF THE PREFERRED EMBODIMENTS

Referring to the drawings, the figures show various aspects of the design, construction, and use of an embodiment of a retained object tag 10 that is used in a system and method of preventing objects from being left inside of a patient's body during a surgical procedure, and that is used in a system and method of detecting the presence of objects once the objects are retained within a patient's body after a surgical procedure is completed. The systems and methods can be designed for integration into the established and normal workflow of operating room procedures and post-surgery procedures, and for minimum interference with these procedures. In different embodiments of the invention, a radiologist or other medical specialist or personnel can visually detect the presence of the retained object tag 10 on a medical image film or workstation, a computer-aided-detection (CAD) technology can detect the presence of the retained object tag in a medical image of suitable format, or both. Furthermore, the systems and methods provide accurate detection of the retained object tag 10 and thus of the object to which the tag is attached, and provide precise locating of the tag and object compared to the known barcoding, RFID, and other technologies. And in some embodiments, the retained object tags 10 can be designed to provide the ability to discriminate and differentiate among different objects.

As used herein, the terms retained object and object refer to objects used in a surgical procedure that may not be readily detected in a medical image such as some surgical implements, sponges, gauzes, towels, cotton balls, operating instruments like surgical needles, and other foreign objects; the term medical image refers to images generated via imaging technologies such as x-ray radiography, computed tomography (CT), magnetic resonance imaging (MRI), ultrasound, nuclear medicine, optical, and the like; and the terms radiolucent and radiopaque refer to detectability, visibility, and identifiability in any of the above-mentioned imaging technologies. Furthermore, the retained object tags and systems and methods described herein are meant for use in human and non-human patients, and are meant for use with tissue that is diseased and that is not diseased.

Figures 1, 2, 3:
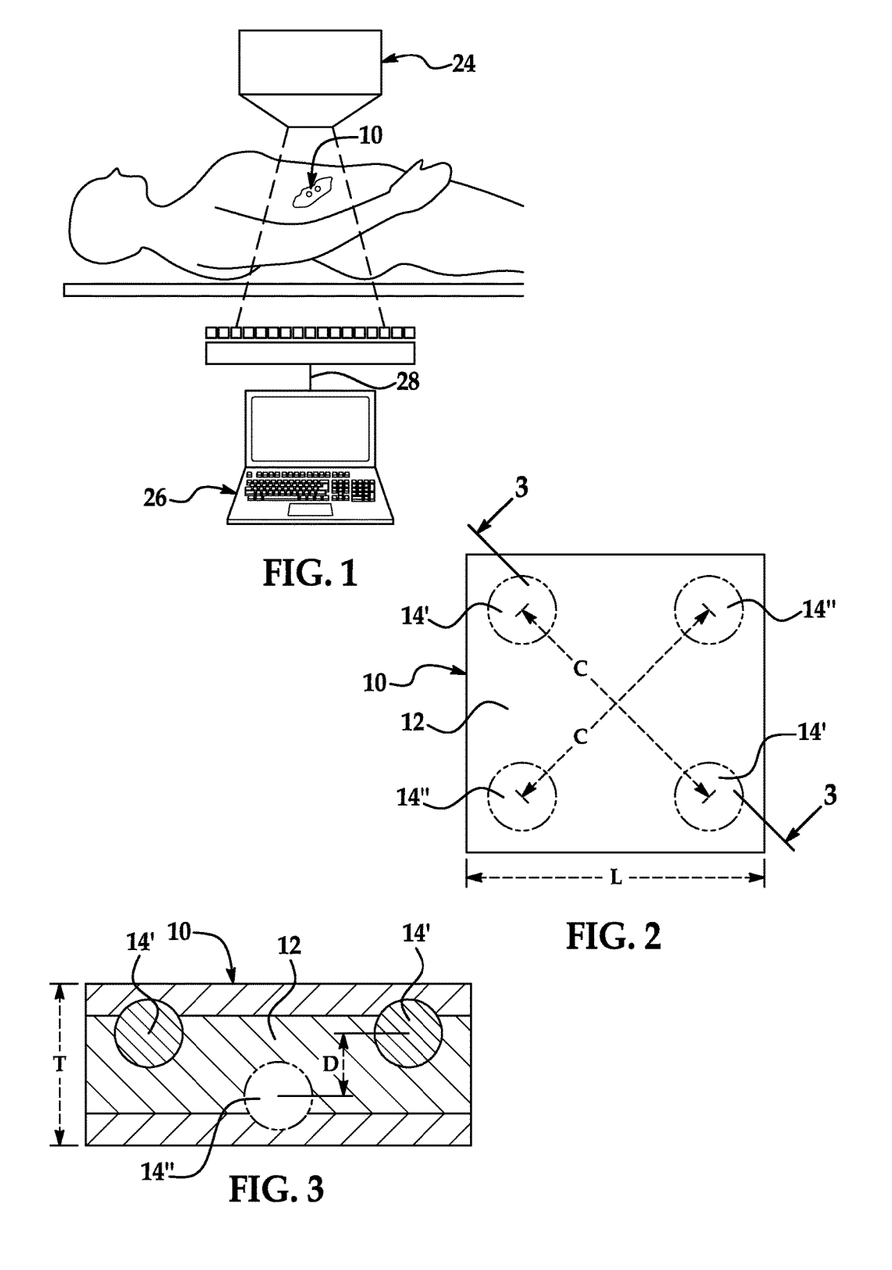
FIG. 1 is a diagrammatic view of an embodiment of a system of detecting a retained object tag.
FIG. 2 is a top view of an embodiment of a retained object tag.
FIG. 3 is a sectional view of the retained object tag, taken at line 3-3 in FIG. 2.

The retained object tag 10 is designed to facilitate manual and computer-aided detection—manual detection via visual inspection of a medical image film by a radiologist or other medical specialist or personnel, and computer-aided detection via CAD programs and software applied to a medical image in suitable format. The retained object tag 10 can be attached to the particular object by adhesion, sewing, staking, press-fitting, molding, implanting, embedding, and other attachment techniques. In application and use, the retained object tag 10 can be a standalone component that is attached to the object by medical personnel in a hospital before or during a surgical procedure, or can be a component that is integrally applied to the object by the original manufacturer. The retained object tag 10 can have different designs, constructions, and arrangements depending upon, among other factors, the object to which it will be attached, and the medical imaging and CAD technologies it will be subjected to. In the embodiment of FIGS. 2 and 3, the retained object tag 10 includes a body 12 and four markers 14', 14" (generally referenced by the numeral 14).

The body 12 carries and secures the markers 14 in place, and directly attaches to the object. The body 12 can be made of a radiolucent material that is substantially transparent in a medical image, and can be made of a biocompatible material. In one example, the body 12 can be made of a polydimethylsiloxane (PDMS) material, an ultra-high-molecular-weight polyurethane (UHME-PE) material, or a polyether ether ketone (PEEK) material; other materials are possible. The body 12 can have different designs, constructions, and arrangements. In one example, the body 12 can have a thickness T of about 1.0 mm or 2.0 mm, and has a total volume that is less than about 10.0 mm$^3$; other thicknesses and volumes are possible. In other embodiments, the body need not be provided and instead the retained object tag could include only the markers, in which case the markers themselves would be directly attached to the object.

The markers 14 are detectable when subjected to medical imaging and CAD technologies. The markers 14, also called micromarkers, can be made of a radiopaque material that is visible in a medical image. In different examples, the markers 14 can be made of a tungsten or tungsten carbide material, a stainless steel material, a gold material, a barium material, or a material with iodinated contrast; other materials are possible. The markers 14 can have different designs, constructions, and arrangements including that shown in the figures in which the markers 14 are three individual spherical beads or microspheres. Some example beads are available from Bal-tec, a division of Micro Surface Engr. Inc., located at 1550 E. Slauson Ave., Los Angeles, Calif., 90011, U.S.A. (www.precisionballs.com); are available from Abbott Ball Company, Inc., located at 19 Railroad Place, West Hartford, Conn., 06110, U.S.A. (www.abbottball.com); and are available from New England Miniature Ball Corp., located at 163 Greenwoods Road West, Norfolk, Conn., 06058, U.S.A. (www.nemb.com); other suppliers and manufacturers are possible. In some cases, the spherical beads are preferred over other shapes of markers because the beads produce the same circular profile image in a medical image, regardless of its orientation relative to the direction(s) of image generation.

In different examples, the beads can have a diameter ranging approximately between 0.20 mm to 2.0 mm, and can have a specific diameter of approximately 0.20 mm, 0.25 mm, 0.40 mm, 0.50 mm, 0.63 mm, 0.70 mm, 0.77 mm, 0.80 mm, 1.0 mm, or 2.0 mm; other diameter values are possible including values greater than or less than those provided here. In at least one experiment, it was found that diameters above 0.80 mm do not provide a significantly meaningful increase in detectability; as described, however, diameters above 0.80 mm are possible, as not all experiments will necessarily yield similar results. An area of an individual bead when projected on a medical image can be approximately less than 1.0 mm$^2$ in some examples, or can have other surface areas. Furthermore, a surface area of an individual bead can be approximately 0.55 mm$^2$ in some examples, or can have other values.

Again referring to FIGS. 2 and 3, in this embodiment the four individual markers are arranged three-dimensionally and are completely encased by the body 12—two from a first set of markers 14' in-line with each other on a first plane, and two from a second set of markers 14" in-line with each other on a second plane. The retained object tag 10 with the first and second set of markers 14', 14" can, for example, be made by the compression molding and microfabrication manufacturing processes subsequently described with reference to FIG. 5; of course other processes not necessarily described herein could be employed to provide the embodiment of FIGS. 2 and 3. The markers 14', 14" are provided in the form of spherical beads. From the top view of FIG. 2, in one example a diagonal centroid-to-centroid distance C can be approximately 2.1 mm; of course this distance can vary as subsequently described with reference to FIGS. 6 and 7, and need not be the same for the markers 14', 14". In the z-axis, and as shown by the sectional view of FIG. 3, a height centroid-to-centroid distance D between the first and second set of markers 14', 14" can be approximately 0.8 mm; again here, the distance can vary as subsequently described with reference to FIGS. 6 and 7. By providing a distance D and a thickness T less than distances C and a length L, the retained object tag 10 has a shorter and flatter construction that may in some cases be more suitable for attachment to a particular object. with side lengths S measured between centers of the spherical beads (i.e., centroid-to-centroid).

The retained object tag 10 is designed such that the markers 14 possess one or more known and pre-determined properties that the CAD technologies can be programmed or otherwise instructed to detect and identify, as is discussed in greater detail below. The pre-determined properties can be a property that would not otherwise be naturally and ordinarily found in a medical image of a human or animal body so that the visual inspector or CAD technologies can detect the markers 14 without a substantial risk of providing false positives and in some cases with no risk at all. In the illustrated embodiment, the pre-determined property can be a pre-determined geometric property such as the diameter of the beads, an intersphere spacing among the beads, the circumference of the beads, the spherical or non-spherical shape of the beads, the curvature of the beads, the surface texture or roughness or smoothness of the beads, or a combination thereof. In these examples and others, the pre-determined geometric property can be based on a property of an individual marker, on geometric relationships between and among the markers, on geometric relationships between and among the markers and the body, or a combination thereof. Other pre-determined properties can include the number of individual markers provided, the shape and size of an individual marker, the shape made by a set of arranged markers, the eccentricity of an individual marker or a set of markers, the symmetry or asymmetry of an individual marker or a set of markers, or the attenuation of the imaging technology passed through a marker. Still, other pre-determined properties are possible.

Furthermore, retained object tags 10 for different objects can have different pre-determined properties so that the CAD technologies can discriminate and differentiate among the objects and communicate this information as output to the user. In one general example, an object A can have a retained object tag possessing a pre-determined geometric property A', and an object B can have a retained object tag possessing a pre-determined geometric property B'. Once detected by CAD processing, the detected geometric property can be matched with a stored or otherwise retrievable pre-determined geometric property A', B' to respectively represent object A, B. In a more specific example, a sponge can be equipped with a retained object tag 10 having markers 14', 14" in the embodiment shown in FIGS. 2 and 3, and likewise a gauze can be equipped with a retained object tag similar to that of FIGS. 2 and 3. The beads of the sponge can have a diameter A, and the beads of the gauze can have a diameter B that is greater than diameter A. The diameters of the beads can constitute the pre-determined geometric property in this example, and the CAD technologies would then be programmed to detect the diameters, and correspond and match detected diameter A with a stored diameter A representing the sponge, and correspond and match detected diameter B with a stored diameter B representing the gauze. The user would then know whether an object left inside a patient's body was a sponge or gauze based on the detected diameter of the accompanying beads.

Figure 4:
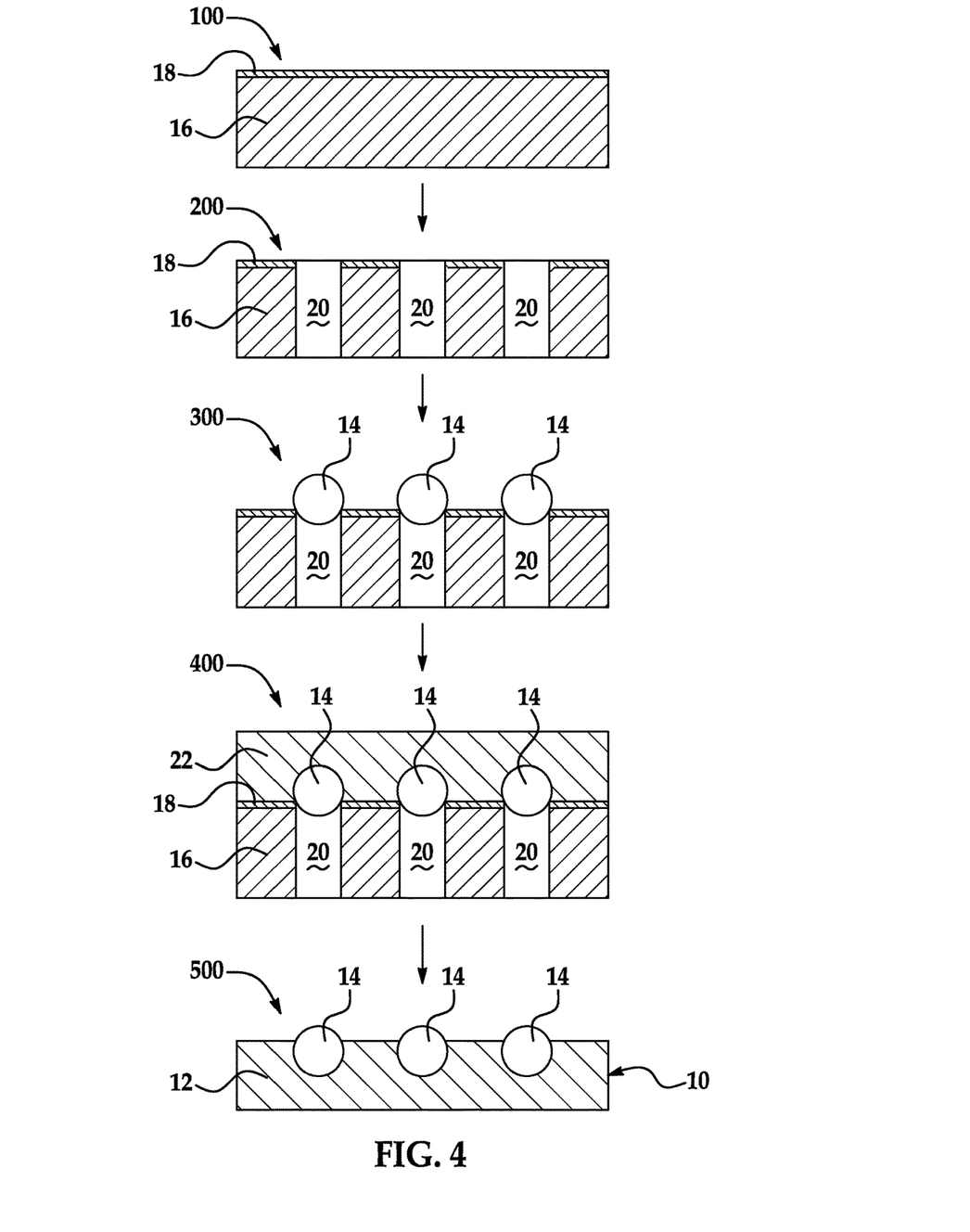
FIG. 4 is a diagrammatic view showing some steps of an embodiment of a method of making a retained object tag.

The retained object tag 10 can be made by different manufacturing processes and steps, depending in part upon the particular materials selected for the markers 14 and the size and shape of the markers, among other considerations. Referring now to FIG. 4, in this example the retained object tag 10 is made by a microfabrication manufacturing process. In a first step 100, a mold substrate 16 of a silicon material is provided, and a 2 µm thick silicon dioxide film 18, or sacrificial layer, is applied over the mold substrate by a plasma-enhanced chemical vapor deposition (PECVD) process. In a second step 200, cylindrical cavities 20 are produced in the mold substrate 16. The cylindrical cavities 20 can have a diameter that is 20 µm less than the diameter of the bead to be used in the retained object tag 10. A photolithography process is used to place an appropriate pattern on the silicon dioxide film 18, a reactive-ion etching (RIE) is applied to the film, and a deep reactive-ion etching (DRIE) process is used to produce the cylindrical cavities 20. The resulting assembly can then be treated with trimethylchlorosilane vapors to minimize or altogether eliminate stiction during the subsequent molding step. In a third step 300, the markers 14 (in this case the beads) are placed in the cylindrical cavities 20. In a fourth step 400, an approximately 2 mm thick layer of a PDMS material 22 (1:10 curing agent to base polymer ratio) is poured onto the mold substrate 16 and over one side of the markers 14, and is allowed to cure and solidify at room temperature for approximately twenty-four hours. And in a fifth step 500, after complete solidification the body 12 and embedded markers 14 are removed from the mold substrate 16 and can be cut and otherwise formed to size as desired. In other embodiments, non-microfabrication processes can be used to manufacture the retained object tag 10.

Figure 5:
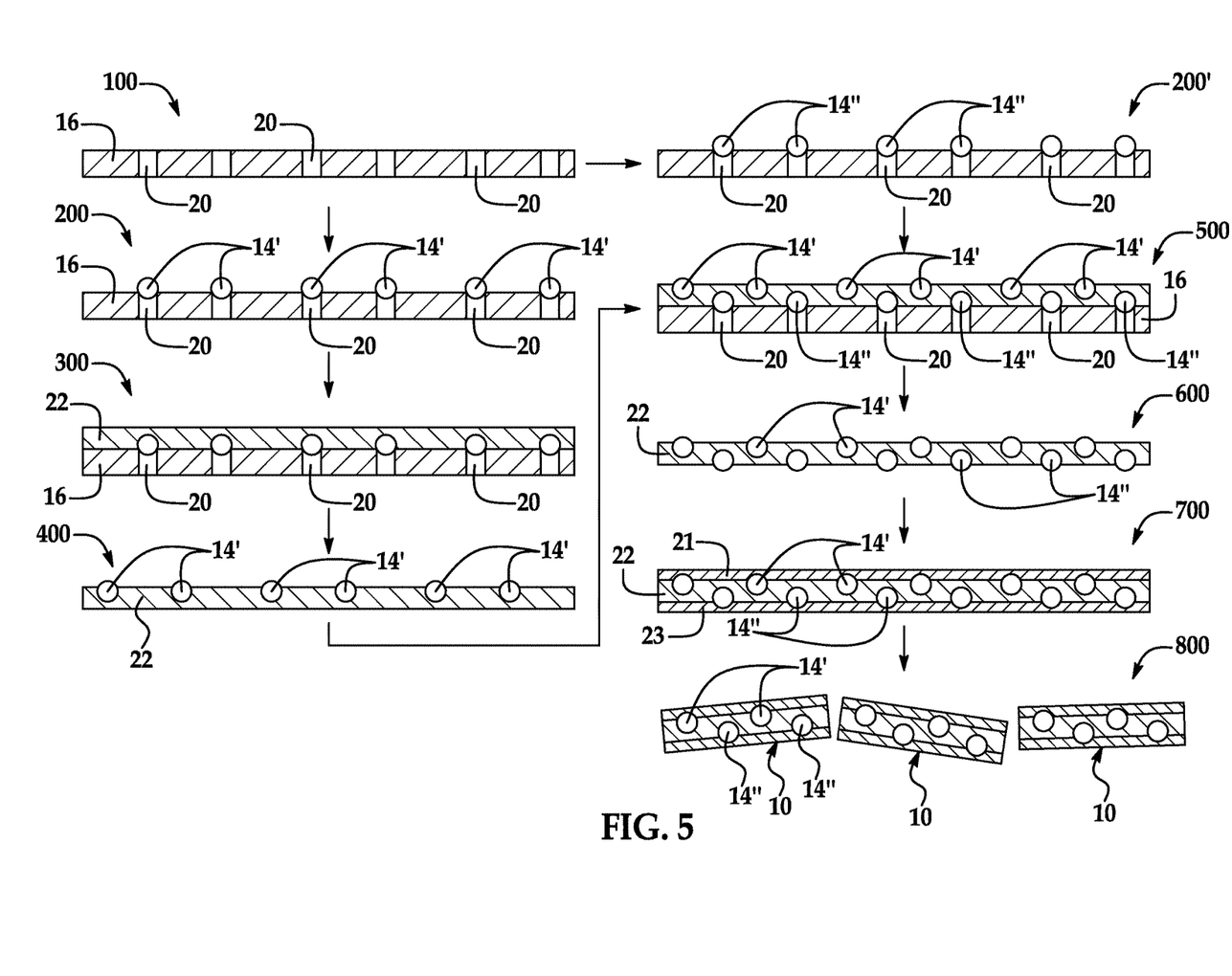
FIG. 5 is a diagrammatic view showing some steps of another embodiment of a method of making a retained object tag.

Referring now to FIG. 5, in another example, another embodiment of the retained object tag 10 is made by compression molding and a microfabrication manufacturing process. This example is in some ways similar to the previous example of FIG. 4. Referring in particular to FIG. 5, in a first step 100 a mold substrate 16 is provided. The mold substrate 16 can be composed of a silicon material, and can be produced by the same steps as described above in the example of FIG. 4. Or, the mold substrate 16 can be composed of a metal material like aluminum, and can be produced by metalworking steps such as drilling; still other materials and production steps are possible. As before, the mold substrate 16 has a number of cavities 20 sized suitably to receive the markers 14 and temporarily hold them in place. To better retain the markers 14, each of the cavities 20 can have a funnel-like or cone-like shape with its mouth of widest extent initially receiving an individual marker. In a second step 200, the first set of markers 14' (in this case a first set of beads) is placed in the cavities 20. The first set of beads can be laid on a top surface of the mold substrate 16 and can find their way to the cavities via vibration or other movement of the substrate. Because the beads are spherical, they can easily roll into the cavities. To help ensure proper placement, a vacuum can be applied at a bottom surface of the mold substrate to draw the beads into the cavities. For markers of different shapes, other placement steps are possible. Concurrently, in a second step 200', the second set of markers 14" (in this case a second set of beads) is placed in the cavities 20 of the mold substrate 16 at another section of the substrate, or at an altogether discrete substrate than that of the step 200. The second set of beads can be placed in the same way as previously described.

Still referring to FIG. 5, in a third step 300 a molten layer 22 of thermoplastic material is brought against the mold substrate 16 and over an exposed side of the first set of beads via a compression molding process. The layer 22 can have a thickness of approximately 1.0 mm and can be composed of a UHME-PE material or a PEEK material; other thicknesses and materials are possible. In a fourth step 400, the layer 22 is solidified and it, and its resultantly embedded first set of markers 14', are removed from the mold substrate 16. At this point, the solidified layer 22 constitutes a portion of the ultimately-formed body 12. In a fifth step 500, the layer 22 and markers 14' are then brought to the other section of the mold substrate 16 where the second set of markers 14" are in place. The layer 22 is turned over so that a side of the layer opposite the first set of markers 14' confronts the second set of markers 14". The layer 22 is then compression molded against the second set of markers 14" which are embedded in the layer. In a sixth step 600, the layer 22 is again solidified and removed from the mold substrate 16. In a seventh step 700, a first layer 21 is bonded to one side of the layer 22 and a second layer 23 is bonded to the other side of the layer 22. The bonding can be performed via compression molding, or via another bonding or molding technique. Together, the layers 21, 22, 23 completely surround and encase the markers 14', 14". And in a final eighth step 800, the one-piece layers 21, 22, 23 are severed into separate pieces to form individual retained object tags 10.

Figure 6:
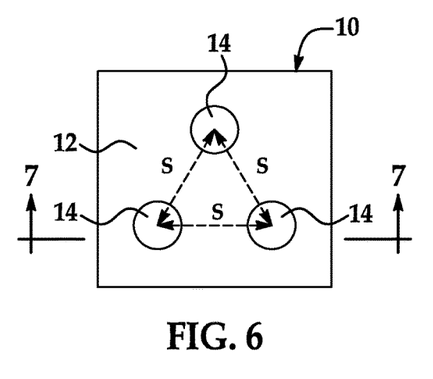
FIG. 6 is a top view of another embodiment of a retained object tag.
Figure 7:
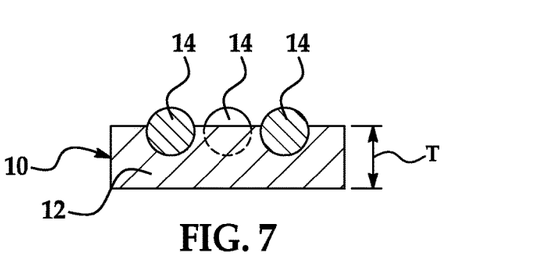
FIG. 7 is a sectional view of the retained object tag, taken at line 7-7 in FIG. 6.

FIGS. 6 and 7 show another embodiment of the retained object tag 10 in which the markers 14 are coplanar and are arranged in an equilateral triangular shape. In different examples, the triangular shape can have side lengths (i.e., intersphere spacing) ranging approximately between 1.0 mm to 2.5 mm, and can have a specific side length of approximately 1.0 mm, 1.3 mm, 1.5 mm, 2.0 mm, 2.1 mm, or 2.5 mm; other side length values are possible including values greater than or less than those provided here. Still, in other examples, lengths between outer surfaces of the spheres (i.e., edge-to-edge spacing) can be approximately 1.3 mm or 2.0 mm, or can range therebetween; other edge-to-edge spacing values are possible including values greater than or less than those provided here. In general, and referring to all embodiments of the retained object tag, the exact materials selected, diameter values selected, side length values selected, and edge-to-edge spacing values selected for the markers will depend upon, among other factors, their visibility in a medical image film and their detectability by CAD technologies.

In other embodiments not necessarily shown in the figures, the markers 14 can have different designs, shapes, constructions, and arrangements, depending in part upon their visibility in a medical image film, their detectability by CAD technologies, and their manufacturability, among other considerations. For example, a single spherical bead could be provided as the marker 14 for the retained object tag 10. Individual markers 14 could be shaped as cubes, pyramids, discs, squares, rectangles, triangles, stars, and the like. In one specific example, a single cube could be provided as the marker 14 for the retained object tag 10, with a side face area or side length as the accompanying pre-determined property. Further, any number of markers 14 could be arranged and patterned in three-dimensional shapes such as a cube shape, a sphere shape, a pyramid shape, and the like. Likewise, any number of markers 14 could be arranged and patterned in two-dimensional coplanar shapes such as a circle shape, a square shape, a rectangle shape, a quadrangle shape, and the like. In the example three-dimensional and two-dimensional shapes, the accompanying pre-determined property or properties could be individual marker sizes and shapes, inter-marker spacings, side lengths, and the like.

Figure 8A:
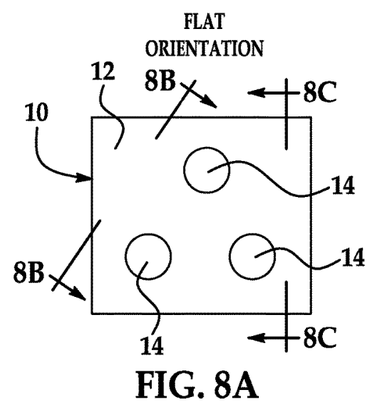
Figure 8B:
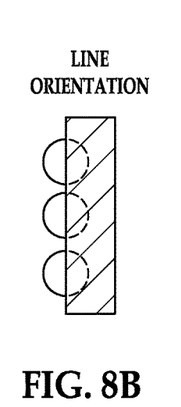
FIG. 8B shows a line orientation as viewed from arrows B-B in FIG. 8A.
Figure 8C:
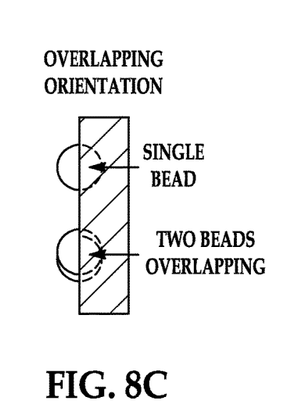
FIG. 8C shows an overlapping orientation as viewed from arrows C-C in FIG. 8A.

For the embodiment of FIGS. 6 and 7 in which the markers 14 are three individual spherical beads arranged in an equilateral triangular shape, experiments were performed to determine the visibility and detectability when the markers 14 are orientated differently with respect to the direction of the associated medical image beam. In the experiment, the beads were made of a tungsten carbide material and x-ray image technology was employed by way of a Siemens Aristos FX radiographic machine. Referring to FIGS. 8A-8C, the markers 14 in the form of beads were spaced apart from one another (centroid-to-centroid) by 2.0 mm in the experiment. X-ray images were generated when the markers 14 had a flat orientation in which the x-ray beam was directed substantially orthogonal to the shared plane of the markers (FIG. 8A); x-ray images were generated when the markers had a line orientation in which the x-ray beam was directed substantially in parallel to the shared plane of the markers with no overlapping markers (FIG. 8B); and x-ray images were generated when the markers had an overlapping orientation in which the x-ray beam was directed substantially in parallel to the shared plane of the markers with two markers in substantial alignment and overlapping each other (FIG. 8C).

Figure 9:
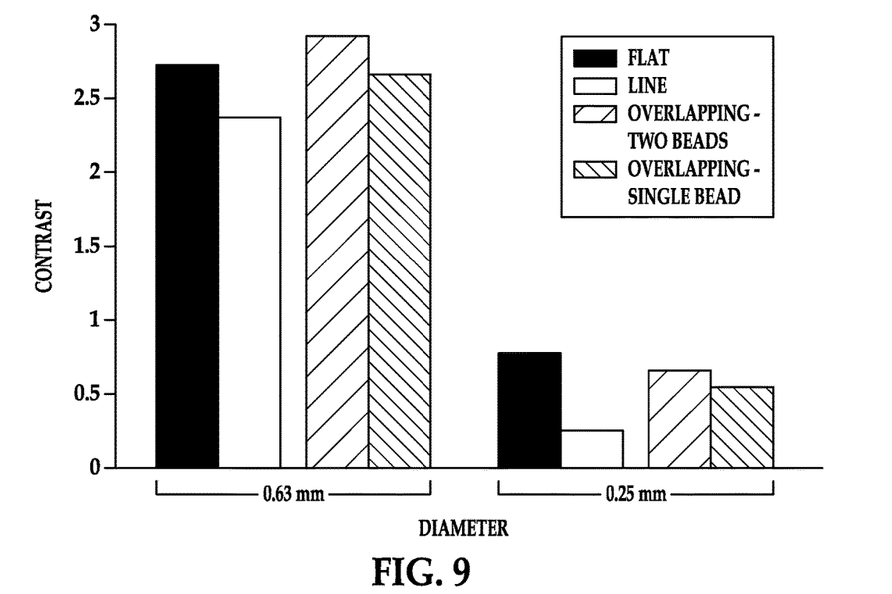
FIG. 9 is a graph showing image contrast quality values of the retained object tag of FIG. 6, having different diameters and in the orientations in FIGS. 8A-8C.

FIG. 9 depicts a graph showing image contrast quality values of the markers 14 with diameters of 0.63 mm and 0.25 mm, and with the markers in flat, line, and overlapping orientations as described immediately above with reference to FIGS. 8A-8C. In the overlapping orientation, image contrast quality values are provided for the two markers 14 that are overlapped ("Two bead"), and for the single marker that is not overlapped ("Single bead"). In the experiment, the x-ray images were analyzed using Metamorph® Microscopy Automation & Image Analysis software provided by Molecular Devices, LLC. Using the software, the image contrast quality values were computed by subtracting the average bead intensity and the average background intensity, and dividing that result by the average background intensity. The greater the contrast quality value, the greater the visibility and detectability. The experimental results shown in the graph of FIG. 9 were deemed acceptable for visibility and detectability.

Figure 10:
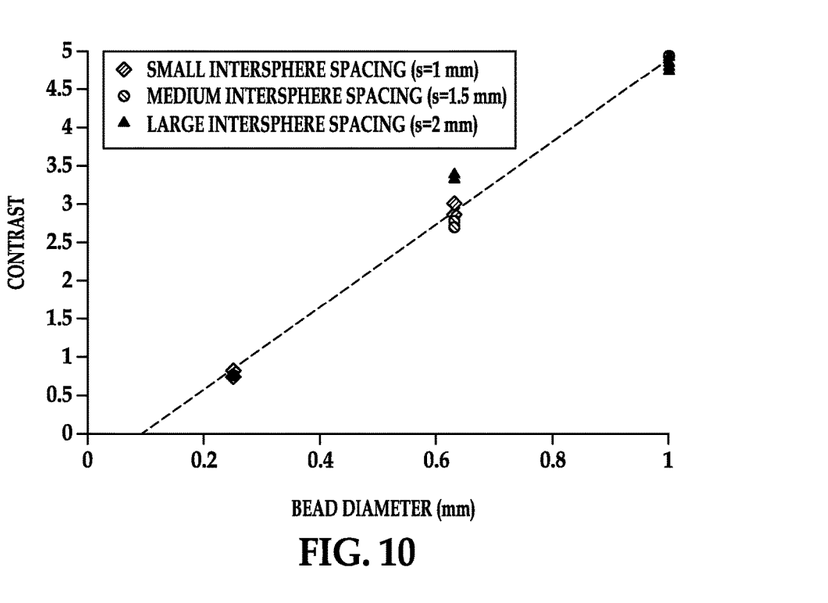
FIG. 10 is a graph showing image contrast quality values versus diameters of retained object tags.
Figure 11:
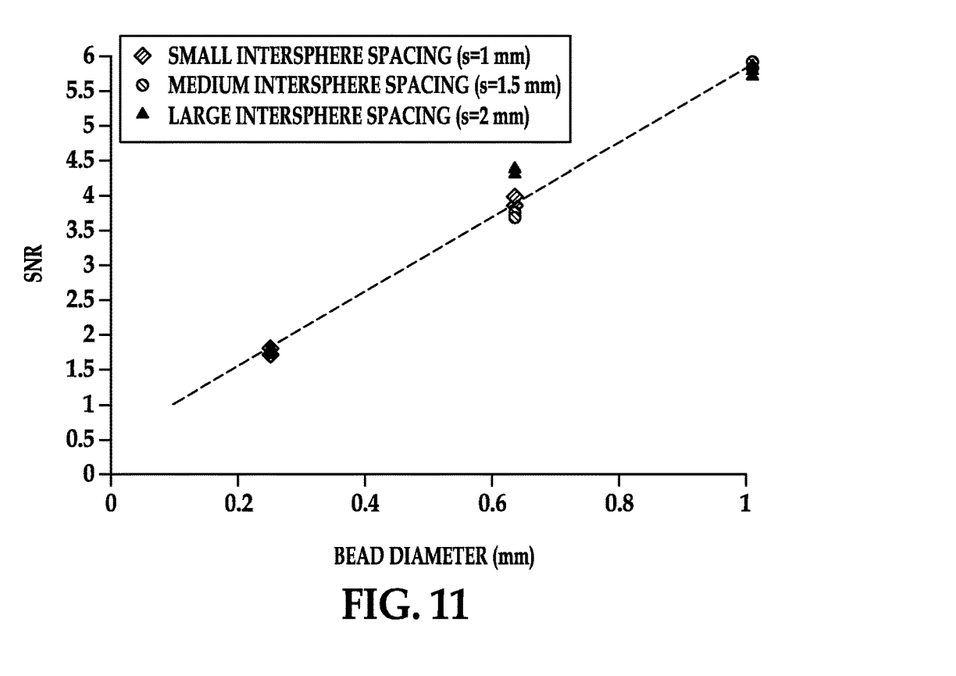
FIG. 11 is a graph showing signal-to-noise ratios (SNR) versus diameters of retained object tags.

Additional experiments were performed to determine the visibility and detectability of the retained object tag 10. FIGS. 10 and 11 are graphs respectively showing image contrast quality values (CONTRAST) and signal-to-noise ratios (SNR) for markers 14 of different diameters. Using the Metamorph® software, the SNRs were computed by dividing the average bead intensity by the average background intensity. The greater the SNR value, the greater the visibility and detectability. Again, the markers 14 are three individual spherical beads arranged in an equilateral triangular shape, and a Siemens Aristo FX radiographic machine was employed. The beads had a flat orientation; were made of tungsten carbide; had diameters of 0.25 mm, 0.63 mm, and 1.0 mm; and had intersphere spacings of 1.0 mm, 1.5 mm, and 2.0 mm. In FIGS. 10 and 11, although the results vary slightly, there is not a substantially measurable image contrast quality or SNR difference among the beads of intersphere spacing of 1.0 mm, 1.5 mm, and 2.0 mm and having a diameter of 0.25 mm. This is also true among the beads of the intersphere spacings having a diameter of 1.0 mm. For the beads having a diameter of 0.63 mm, however, the beads with an intersphere spacing of 2.0 mm have the greatest image contrast quality value and signal-to-noise ratio, while the beads with an intersphere spacing of 1.5 mm have the least. The beads with an intersphere spacing of 1.0 mm and diameter of 0.63 mm have an image contrast quality value and signal-to-noise ratio that falls between the other two intersphere spacings.

Figure 12:
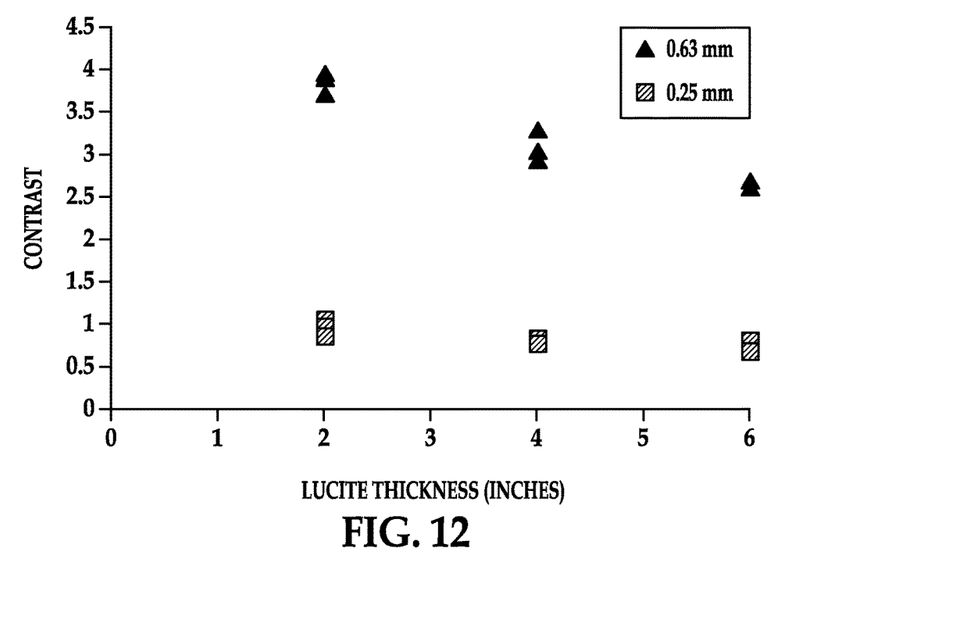
FIG. 12 is a graph showing image contrast quality values versus thicknesses of a Lucite material used in experimentation to simulate human soft tissues.

FIG. 12 is a graph showing image contrast quality values against thicknesses of 2.0 inches, 4.0 inches, and 6.0 inches of Lucite material. The Lucite material was used to simulate the effect of human soft tissues. Again, the markers 14 are three individual spherical beads arranged in an equilateral triangular shape as in FIGS. 6 and 7, and a Siemens Aristo FX radiographic machine was employed. The beads were made of tungsten carbide and had diameters of 0.25 mm and 0.63 mm. The beads having a diameter of 0.63 mm—while steadily decreasing in image contrast quality with Lucite thickness—have somewhat significantly better image contrast quality values than those having a diameter of 0.25 mm. It should be appreciated that not all experiments will yield the exact results of FIGS. 9-12.

Figure 13:
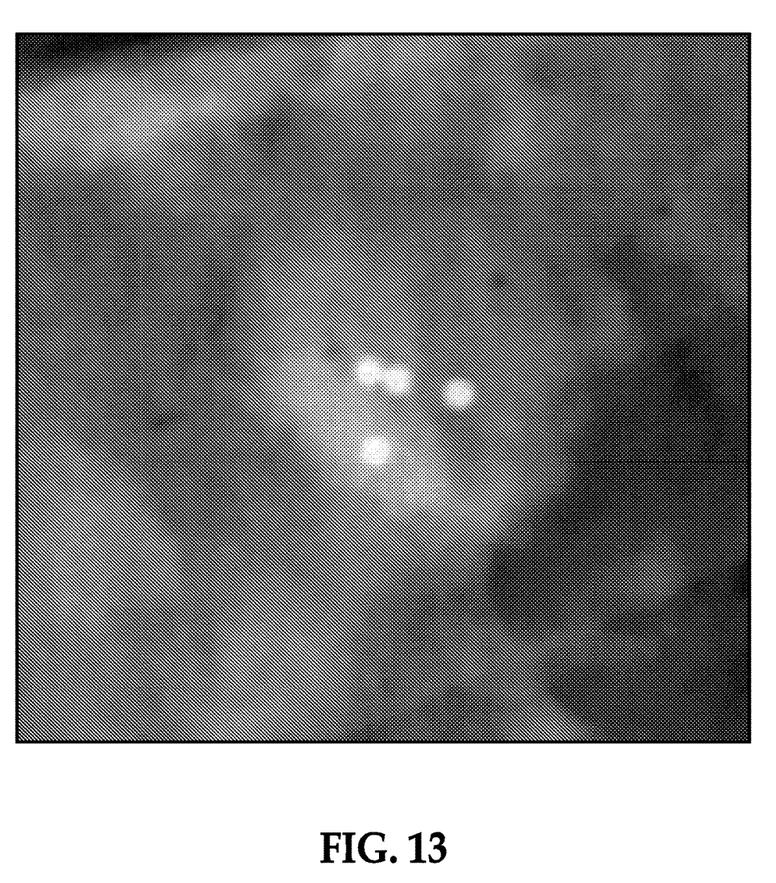
FIG. 13 is an x-ray image of an embodiment of a retained object tag.

Furthermore, it has been determined that the retained object tag 10 can be designed, constructed, and arranged in ways to facilitate and contribute to its manual and computer-aided detection. For instance, whatever its design and construction and arrangement, it has been found that a retained object tag with four or more pre-determined properties can in some cases be more detectable than a retained object tag with less than four pre-determined properties. This is partly because most medical imaging technologies convert three-dimensional spaces to two-dimensional images, and therefore some pre-determined properties can be hidden and obscured in the images when taken at certain orientations. A retained object tag with four or more pre-determined properties may maintain its detectability to a desirable extent in a two-dimensional image at all orientations. One example of this is the three-dimensional pyramid shape shown in the x-ray image of FIG. 13. The pyramid shape could be a tetrahedron. The pyramid retained object tag is made up of four spherical beads, with three beads making up its triangular base and one bead at its apex. In FIG. 13, the four spherical beads are the four white dots shown near one another at an approximate center of the x-ray image. Some pre-determined properties in this example are geometric properties and could be the six line edges extending between the beads of the pyramid, or the four side faces of the pyramid. With the six line edges, even when the pyramid's triangular base is imaged and viewed as an overlapped single line, three of the six line edges are still detectable. Another three-dimensional shape with four or more similar pre-determined geometric properties includes the previously-mentioned cube shape, which would include eight markers making up the shape, twelve line edges, and six side faces. Of course, retained object tags with less than four pre-determined properties are still suitable in some examples.

Another trait that has been found to facilitate and contribute to manual and computer-aided detection—despite tag orientation in a medical image—is spacing among the markers 14 of the retained object tag 10. If the spacing is insufficient and the markers 14 are physically too close together, the markers can overlap and appear as a single line or single object in a medical image. When this occurs, the detectability of the retained object tag 10 is oftentimes diminished. It has been found that spacing distances among the markers 14 that are greater than a largest cross-wise dimension of the individual markers can reduce or altogether preclude overlap and the attendant single line or single object generation, and can therefore maintain sufficient detectability. In the example of the pyramid retained object tag, the largest dimension of the individual spherical beads is their diameters. Hence, if the beads are spaced apart edge-to-edge by a distance that is greater than the diameter of the spherical beads, one or more of the beads will remain free of overlapping at a particular orientation, providing a space between the non-overlapped bead(s) and the overlapped ones. The detectability of the retained object tag 10 is therefore maintained. Of course, retained object tags with spacing that is not greater than a largest dimension of the individual markers are still suitable in some examples.

The exact spacing distance can vary in different retained object tags and may depend upon, among other factors, the magnification level of the imaging technology and the region of the human or animal body that is to be imaged. For example, it can be more challenging to detect the retained object tag 10 in a region of a human body that is more radiopaque than other regions. In particular, it has been found that some anatomical structures can be problematically-radiopaque and, when overlaid by the retained object tag 10 in a medical image like an x-ray, can diminish the detectability of the tag. At least some of these anatomical structures are located in the abdomen and pelvic region of a human body, and include the ileopectineal line, the ilioischial line, the femoral head and neck, the sacroiliac joint, the vertebral body edges, the pelvic brim, and the spinous process. The listed anatomical structures were observed through experimentation with cadavers. Of course, other problematic anatomical structures are likely, including structures from other regions of the human body. The approximate size and dimensions of the listed anatomical structures were measured on the test cadavers. The spacing distances among the markers 14 in the retained object tag 10 were then provided as greater than the largest measured size and dimension of the anatomical structures. In subsequent experimentation, the retained object tag 10 with the greater-spaced markers 14 were detectable when overlaid at the anatomical structures since at least one of the markers was located remote of the structures and not overlaid by them. Accordingly, in order to help ensure detectability in some embodiments, spacing distances among the markers in a retained object tag may be based on and made greater than the expected size and dimension of potentially problematically-radiopaque anatomical structures to be imaged.

Yet another trait that has been found to facilitate and contribute to manual and computer-aided detection—despite tag orientation in a medical image—is symmetry in the retained object tag 10. Since symmetrical traits are not always naturally and ordinarily found in a medical image of a human or animal body, the visual inspector or CAD technology can readily detect the symmetrical traits without a substantial risk of false positives and in some case with no risk at all. The pre-determined properties can be symmetrical traits of the retained object tag 10. In the example of the pyramid retained object tag, its six line edges can have congruent length dimensions, congruent angles, or both, constituting symmetrical traits in the tag. The congruent length dimensions repeat six times, adding to its detectability. So when the pyramid's triangular base is imaged and viewed as an overlapped single line, for instance, three of the six congruent and repeating line edges are still detectable. It has been found that two or more repeating symmetrical traits, such as length dimensions and angles, can facilitate and contribute to computer-aided detection of the retained object tag 10. Of course, symmetry and repetition is present in other shapes, including the previously-mentioned cube shape which possesses symmetry and repetition among its line edges and side faces.

As briefly described above, the retained object tag 10—in addition to, or instead of, being visually detected on a medical image film or screen by a radiologist or other medical specialist or personnel—can be detected by computer-aided-detection (CAD) technologies and systems. The medical images generated by a medical imaging machine can be provided to the CAD technologies in a digital or other suitable and compatible format for processing. The CAD technologies and processing can be incorporated into or a part of a Patient Archiving and Communication System (PACS) commonly used in hospitals, for example, can be automated or selectively performed, and can be supported on a dedicated or shared computer, tablet, or other electronic device. In the embodiment of FIG. 1, an x-ray machine 24 is connected directly to a computer 26 via a hardwire 28, and hence the CAD technologies supported on the computer receive the x-ray image via the hardwire. Other ways of communicating a generated medical image to a computer or other electronic device are possible, including by transferring the image to the computer via a data storage device such as a USB flash drive, via network communications, or via wireless communications.

Algorithms can be formulated and coded on MATLAB®, for example, to perform the functionality of detecting the pre-determined properties of the retained object tag 10, of the markers 14, or of both; or other programming languages can be used including C or C++. The programming can be stored on a computer readable medium that includes a non-transient data storage device. In one general example, a first set of medical image processing algorithms and functions is applied to the entire medical image. The first set removes and filters attenuations and properties such as geometric properties that are unlike those of the tag 10 and/or the markers 14; the removed properties can include osseous features, bone edges, noise, and extreme attenuations. A second set of medical image processing algorithms and functions detects and identifies potential sites of the tag 10 in the medical image by matching the pre-determined properties of the tag and/or the markers 14 with approximately or closely equal properties found in the medical image. A third set of medical image processing algorithms and functions is then applied to match stored or otherwise retrievable pre-determined property information and data of the tag and/or markers with the detected properties in the medical image. Once matched, the CAD technologies can communicate the output to the user.

Figure 14:
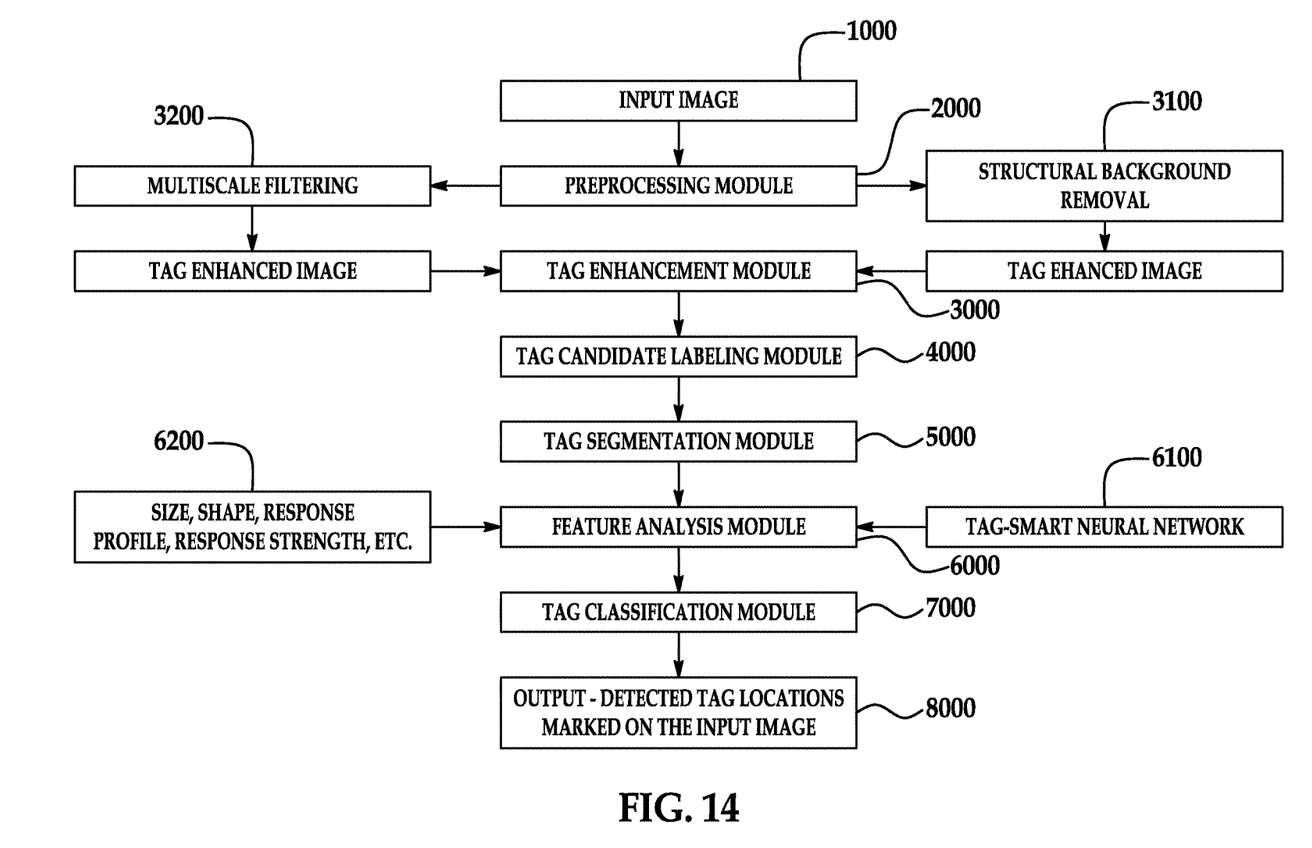
FIG. 14 is a flowchart showing one embodiment of a computer-aided-detection (CAD) method for detecting the presence of a retained object tag in a medical image.

In a more specific example shown by the flowchart of FIG. 14, one embodiment of a computer-aided-detection method and system is represented by multiple steps in which different functions are performed. In other embodiments, more, less, or different steps can be performed in the computer-aided-detection method, or the steps depicted in the figure could be performed in a different order. Indeed, the steps performed may be dictated by the particular medical imaging machine, the medical image's format, and the retained object tag and its pre-determined properties, among other possible factors.

In a first step 1000 of FIG. 14, one or more medical images are inputted to and received by the CAD technologies in order to initiate the method. As previously described, the medical image can be transferred in a suitable format for processing via a hardwire connection, a data storage device, a network or wireless communication, or via another way. In a second step 2000, a preprocessing module or function is performed. In one example, the preprocessing function is applied to the medical image in order to remove image artifacts that may exist in the medical image. This could include collimator shadows, for example. If required, the preprocessing function may also reformat the medical image to a suitable and compatible format for further processing.

In a third step 3000, a tag enhancement module or function is performed. The tag enhancement function generally enhances the detectability of the retained object tags for further processing. One instance of enhancing detectability is by augmenting signal strength of the retained object tag. And like other steps in the computer-aided-detection method, the function of this step can be achieved in different ways. In a first example, the tag enhancement function involves removing or suppressing structured background items, step 3100. In this step, noise effects that may have been created by the medical imaging technology and that may exist in the medical image are reduced or altogether removed. Taking an x-ray medical image as an example, noise can be caused by associated quanta and by an accompanying image recording device such as a flat panel detector. In one way the structured background items are removed via a band-pass filter configured to have a maximum response approximately matching the retained object tag, the markers, or both. In another way the structured background items are removed by i) enhancing the retained object tag through matched filtering in which a known signal, or template, of the tag can be incorporated into a kernel adaptive filter in order to maximize a response indicating the possible presence of the tag; and ii) removing potential sites of retained object tags in the medical image by linear or non-linear filtering such as via a large kernel Gaussian filter, a large kernel box filter, or a median filter. After this, the result of ii) is then subtracted from i), yielding a medical image with enhanced potential retained object tag sites where structured background items are removed and where the tags' signal strength is augmented.

In a second example, the tag enhancement function involves multiscale filtering or processing and object response extraction, step 3200. This step can be suitable in circumstances in which magnification levels of the retained object tag 10 will vary in the medical image generated; the degree of magnification, or even absence of it, in a medical image may depend upon the particular surgical procedure being performed, the medical imaging machine and technology employed, and other factors. The multiscale filter can be configured with scales to account for potential levels of magnification of the retained object tag 10 and hence size of the tag, and to ultimately provide detectability enhancement. In a circumstance in which the magnification level is constant, the multiscale filter can be configured with a single scale. The medical image can be processed via Gaussian filtering with a suitable Gaussian kernel based on expected magnification and tag size, and an object response value can be derived at each pixel of the medical image from eigenvalues of a Hessian matrix containing second-order partial derivatives at the respective pixel. Multiscale responses can then be determined at each pixel. The resulting response at each pixel can be taken as the weighted sum of the multiscale responses, as the maximum response of the multiscale responses, or can be determined in another way.

Still, the tag enhancement function can enhance the detectability of the retained object tags in other ways. In yet another example, known and expected anatomical structures that are unlike the pre-determined properties of the retained object tag 10 can be removed or suppressed. The precise anatomical structures will depend on the region of the human or animal body being imaged, and may include structures such as bones, bone edges, larger calcifications, organs, other objects intentionally present, and the like. Removal can be achieved via morphological image filtering or processing of the anatomical structures in which the medical image is subject to dilation and erosion. The morphological image filter can be configured with structuring elements that match items with dimensions and sizes of the known anatomical structures. The known anatomical structures are hence removed, while the retained object tags 10 are retained. In one specific example, the morphological image filter can be configured to remove items that are thin and elongated like a bone edge; this configuration would not remove the retained object tag 10 in an embodiment in which the tag and its pre-determined properties are not correspondingly thin and elongated. Furthermore, the medical image can be filtered at different orientations in order to remove bone edges following different paths. And yet another example of enhancing detectability of the retained object tags also involves morphological image filtering, but is configured with structuring elements that match items with dimensions and sizes of the retained object tag 10 and its pre-determined properties. One way of accomplishing this is by utilizing a top-hat filter. In an embodiment in which the markers 14 are beads, the structuring element can match the dimension and size of the beads or of the pre-determined properties of the beads. The examples described for enhancing the detectability of the retained object tags—and other ways not described—can be performed alone or in combination during the tag enhancement function. Lastly, the resulting enhanced and augmented retained object tags can be combined such as by a weighted sum operation in order to yield a weighted-enhanced and -augmented tag image.

In a fourth step 4000, a tag candidate labeling module or function is performed. The tag candidate labeling function generally identifies potential sites in the medical image in which retained object tags may be present. In one example, the pixel response values of the previous tag enhancement function can represent the possibility that a tag is indeed present at a potential site—the higher the response value, the higher the possibility. To identify high pixel response values, the tag candidate labeling function can process a histogram or other data distribution of the response values and distinguish those above a set threshold value. The threshold value may be fixed, or may be set iteratively and adaptively by initially setting the threshold value at a higher value and determining the number of potential tag sites at that value. In the iterative example, each of the potential tag sites can then be subject to a segmentation function such as the one subsequently described. If the number of potential tag sites is below a criterion or criteria range, a new threshold value may be set again. The iteration may carry on until the criterion or criteria range is satisfied.

In a fifth step 5000, a tag segmentation module or function is performed. The tag segmentation function generally further refines the potential tag sites and prepares them for the next step in the computer-aided-detection method. Many object segmentation methods and criteria can be used in the tag segmentation function, including gradient-based or intensity (pixel value) based methods. In one embodiment, the tag segmentation function can utilize mathematical optimization such as a cost function that is determined, for example, by local statistical variation of pixel response values in a limited region surrounding the particular potential tag site; for example, a thirty-one-by-thirty-one pixel region extending from the site's centroid. If an individual pixel satisfies a set connectivity criterion and its response value is above a set adaptive threshold value, the individual pixel is then deemed to constitute and be a part of the potential tag site. The connectivity criterion can be different pixel connectivities including four- or eight-connectivity, and the set adaptive threshold value can be a multiple of the standard deviation of the response values in the limited region or can be determined in another way. The tag segmentation function can cease its performance once all neighboring and adjacent individual pixels that satisfy the set connectivity criterion and adaptive threshold value are connected. The satisfying individual pixels constitute the refined potential tag site.

In a sixth step 6000, a feature analysis module or function is performed. The feature analysis function generally makes an analysis concerning whether a potential tag site is indeed a true retained object tag, and can involve feature extraction. Features of the potential tag sites for the feature analysis function, including its size, shape, texture, response value relative to neighboring background response value, intensity profile, or the like, can be determined and can constitute feature descriptors, step 6200. Another feature descriptor can be maximum or average response values over the potential tag sites from the set of enhanced images of the previous tag enhancement function. Furthermore, in order to facilitate the analysis of whether a potential tag site is indeed a true retained object tag, criteria for feature descriptors can be selected based on, for example, the size and shape of the retained object tag and based on its pre-determined properties. Selection of the criteria may also account for, among other possible considerations, the magnification level of the particular medical image and the direction(s) and projection(s) at which the medical image will be generated.

In one embodiment of the feature analysis function, the features of the potential tag sites can be analyzed via a tag-smart neural network, step 6100. Here, the tag-smart neural network can have an input layer, any number of hidden layers including one or two or more, and an output layer. The layers can contain multiple neurons grouped in arrays, and the neurons of each array between two adjacent layers can be connected by synapses with trained weights. As input, the input layer can use one or more two-dimensional image region-of-interests centered at the potential tag or marker sites. The image region-of-interests can be the set of enhanced images of the previous tag enhancement function, or a subset or superset thereof. The neuron in the output layer can combine weighted responses from the final hidden layer into a checkpoint value. The tag-smart neural network may be trained with many (e.g., thousands) true retained object tags and their pre-determined properties, and with many false positive objects in order to train the neurons to differentiate between true retained object tags and false positives. In this way, the checkpoint value may represent the judgment of the tag-smart neural network concerning the likelihood that the inputted region-of-interest contains a true retained object tag. In one example, the checkpoint value can provide a numeral between zero and one, with the numeral one constituting the highest likelihood that the inputted region-of-interest contains a true retained object tag and the numeral zero constituting the lowest likelihood.

In one specific example of training a neural network, a database of medical images with and without a retained object tag was created. The retained object tag had different positions and orientations in the medical images. There were a total of over three-thousand medical images of cadavers with the retained object tag superimposed and overlaid with the cadavers' anatomical structures and background in random ways. The database also includes information about and medical images of man-made objects and surgical implements such as lines, tubes, and needles. Additional medical images containing tags, objects, and the like, can be added to the database or to another database for the purpose of training a neural network. In some cases, approval from an institutional review board will have to be sought for approval concerning patient medical images, and where necessary, this approval was received for the creation of the subject database. The database was used to train a neural network and to provide templates where needed in the computer-aided-detection method.

Furthermore, in the feature analysis function, additional measures can be taken to help determine whether a potential tag site is indeed a true retained object tag. For example, the presence of multiple pre-determined properties in a single retained object tag can be used to differentiate true retained object tags from false positives. In a specific example, a particular retained object tag is a tetrahedron with four of its markers at its apices taken as pre-determined properties. The distance between the markers can have a dimension of 3.0 mm, and the medical imaging technology can generate a medical image with a magnification level of two. Therefore, in this specific example, one feature descriptor and criterion for a potential tag site being deemed a true retained object tag can be the presence of two, three, or more adjacent markers with a spacing of approximately 6.0 mm. Moreover, this criterion can be used in combination with other criteria.

Still, other feature descriptors and criteria can be used in the feature analysis function to facilitate the determination of whether a potential tag site is indeed a true retained object tag. In one example, spacing distances between markers can serve as a criterion. Here, a square root of the sum of the squares of spacing distances between all the centroids of the markers can be calculated. A range of values of this calculation can be determined by accounting for the level of magnification for a particular medical image technology. The calculation can be performed for a potential tag site, and falling within and satisfying the range can help further ensure that the potential tag site is indeed a true retained object tag. In another example, similarity of shapes between the potential tag site and a true retained object tag can serve as a criterion. This can involve determining whether the potential tag site matches possible shape variances of a true retained object tag when it is imaged from different directions and at different orientations. The shape of a true retained object tag can include the shape of individual markers and the shape of the tag as a whole, as previously described. A shape descriptor in this example may include eccentricity, moments, compactness, sphericity, rectangularity, and the like; and determining similarity may involve measurements such as correlation, dot product, Euclidean distance, and other methods. In yet another example, a gradient filter is applied to the potential tag site and can serve as a criterion. This example would be used in an embodiment in which the retained object tag has markers that are beads. The gradient filter can use a second derivative and can accentuate objects that have a changing intensity at a certain rate. Further, the gradient filter can calculate the change in intensity values of objects in the z-axis, and can accentuate a changing object with first increasing intensity and then decreasing intensity, with a value that corresponds to a surface curvature of the bead. And in yet another example, similarity between the potential tag site and a false positive template can serve as a criterion. The false positive template can include a number of templates in a database containing known false positives such as surgical sutures, metal clips, and other objects. This example can involve the calculation of correlation coefficients, with a high coefficient indicating a high likelihood that the potential tag site matches a false positive template.

In a step 7000, a tag classification module or function is performed. The tag classification function generally makes a final determination of whether a potential tag site is indeed a true retained object tag. Like other functions in the computer-aided-detection method, the tag classification function can be carried out in different ways. For example, some or more of the previously-described analysis of the feature analysis function can be utilized sequentially such as in a decision tree, in parallel such as with logical operations, as input to a trained linear classifier such as a linear discriminant classifier or a simple mathematical combination, or as input to a non-linear classifier such as higher-order classifiers or a trained neural network. In these examples, the criteria and the checkpoint value of the feature analysis function can be used together in order to help finally determine whether a potential tag site is a true retained object tag. In one example, a set of classifiers can be trained to make the determination as a panel. These examples of the tag classification function can be used alone or in combination with one another. Similarly as before, training could involve many (e.g., thousands) of true retained object tags and false positives from a database of live or diseased individuals, for example.

Lastly, in a step 8000, an output function is performed in order to inform a user of previously-identified potential tag sites that have been deemed true retained object tags in the computer-aided-detection method. This information can be conveyed and displayed to the user in different ways. In general, the inputted medical image can be shown with superimposed notations or indicia of the true retained object tags. The display can be on a screen of the particular medical imaging machine, or of a dedicated screen of the computer-aided-detection method such as on a computer, tablet, or other electronic device. The notations or indicia can point to the location of the true retained object tag or otherwise highlight the location via coloring, arrows, triangles, squares, circles, blinking stars, asterisks, and other markings. In one embodiment, the size and/or brightness of the notations or indicia can signify to the user the likelihood that the detected object is a true retained object tag. Still, in other embodiments, the information can be conveyed and displayed to the user on a printed piece of paper. The information can include one or more of the following: the location of the true retained object tag, the type of object (e.g., sponge, gauze), or the degree of likelihood that the identified object is a true retained object tag. And in one embodiment, the output function could inform the user that the quality of the medical image generated is deficient and/or that there is a possibility that a true retained object tag has been detected, and that another medical image should therefore be generated and input to the computer-aided-detection method.

In other embodiments, the computer-aided-detection methods described above can be implemented and performed without the use of a discrete retained object tag. In other words, some objects can themselves possess one or more pre-determined properties detectable by CAD technologies, and need not be equipped with a separate tag or set of markers. For example, surgical needles are conventionally manufactured in standard sizes with known diameters and curvatures of their hollow bodies. The diameters and curvatures could constitute pre-determined geometric properties, and the CAD technologies could be programmed to detect these properties. And in some embodiments, the computer-aided-detection method can operate as a closed black box with its only input being the medical image, or the computer-aided-detection method can receive input from other sources such as from a digital-imaging-and-communications-in-medicine (DICOM) header; input from the DICOM header could include source-to-detector distance of the medical imaging machine, magnification levels, and other information. Furthermore, in other embodiments, the computer-aided-detection method could be designed to receive input from a user concerning a particular object that is suspected of being present in a medical image.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A retained object tag, comprising:
a body comprised of a radiolucent material, said body configured to be attached to a separate object used in a surgical procedure to detect the separate object when the separate object is inadvertently retained in a patient during a surgical procedure;
a first marker carried by said body, said first marker comprised of a radiopaque material;
a second marker carried by said body, said second marker comprised of a radiopaque material; and
a third marker carried by said body, said third marker comprised of a radiopaque material;
wherein said first, second, and third markers are at least partially embedded in said body at positions with respect to one another that provides a space between at least two of said first, second, and third markers when the retained object tag is imaged in a medical image at different orientations, said space facilitating manual and computer aided detection of the retained object tag, wherein at least one of the first, second, and third markers, or a combination thereof, possesses at least one pre-determined geometric property that is detectable via computer-aided detection processing.

2. The retained object tag of claim 1, further comprising a fourth marker carried by said body and comprised of a radiopaque material, wherein said first, second, third, and fourth markers are located in said body in a three-dimensional arrangement.

3. The retained object tag of claim 1, wherein the retained object tag comprises one or more markers in addition to said first, second, and third markers.

4. The retained object tag of claim 3, wherein all of said markers are located in said body at positions with respect to one another to outline an approximate pyramid shape.

5. The retained object tag of claim 1, wherein said first, second, and third markers are respective first, second, and third spherical beads with diameter dimensions ranging between approximately 0.2 mm and 2.0 mm, inclusive.

6. The retained object tag of claim 2, wherein said first, second, third, and fourth markers are respective first, second, third, and fourth spherical beads with diameter dimensions ranging between approximately 0.2 mm and 2.0 mm, inclusive.

7. The retained object tag of claim 3, wherein all of said markers are spherical beads with diameter dimensions ranging between approximately 0.2 mm and 2.0 mm, inclusive.

8. The retained object tag of claim 5, wherein said first, second, and third beads have diameter dimensions that are less than or equal to approximately 1.0 mm.

9. The retained object tag of claim 1, wherein said first, second, and third markers are located in said body at positions with respect to one another that provides a space between adjacent markers taken between respective marker edges that is greater than a largest cross-wise dimension of each of the adjacent markers in order to facilitate manual and computer-aided detection of the retained object tag.

10. A retained object that includes the retained object tag of claim 1.

11. A retained object detection system comprising the retained object of claim 1 and comprising a computer-aided detection system programmed to detect said at least one pre-determined geometric property in a medical image.

12. The retained object detection system of claim 11, wherein said pre-determined geometric property is at least one of: i) an area of at least one of said first, second, and third markers; ii) a shape of at least one of said first, second, and third markers; iii) a cross-wise dimension of at least one of said first, second, and third markers; iv) a diameter of at least one of said first, second, and third markers when said markers are provided as spherical beads; v) a curvature of at least one of said first, second, and third markers when said markers are provided as spherical beads; vi) a distance between centroids of at least two of said first, second, and third markers; or vii) a repetition of at least two of a geometric property among said first, second, and third markers.

13. The retained object detection system of claim 12, wherein said computer-aided detection system comprises an artificial neural network trained to recognize said pre-determined geometric property, said neural network being trained using a plurality of medical images containing the retained object tag at different orientations.

14. The retained object tag of claim 1, wherein, when the retained object tag is projected on a two-dimensional medical image, the retained object tag produces a substantially similar and recognizable appearance that is detectable via manual and computer aided detection regardless of orientation of the retained object tag.

15. A method of detecting the presence of a retained object comprising the retained object tag of claim 1, the retained object tag possessing a pre-determined geometric property in a medical image, the method comprising the steps of:
(a) receiving the medical image;
(b) identifying a potential site in the medical image in which the retained object may be present;
(c) analyzing a feature of the identified potential site against the pre-determined geometric property of the retained object tag;
(d) determining whether the identified potential site is the retained object based at least in part upon the analyzed feature; and
(e) outputting the determination.

16. The method of claim 15, wherein the method detects the presence of the retained object tag in the medical image.

17. The method of claim 16, wherein step (c) further comprises analyzing features of the identified potential site against the pre-determined geometric property of one of the markers, against a pre-determined geometric property possessed between at least two markers.

18. The method of claim 17, wherein the pre-determined geometric property is an area, shape, signal strength, or a combination thereof, of at least one of the markers.

19. The method of claim 17, wherein the markers are spherical beads, and the pre-determined geometric property is a diameter of the spherical beads, a curvature of the spherical beads, or both.

20. The method of claim 17, wherein the pre-determined geometric property is a distance between centroids of at least two markers.

21. The method of claim 17, wherein the pre-determined geometric property is a symmetry possessed by at least one of the markers.

22. The method of claim 16, wherein step (d) further comprises determining whether the identified potential site is the retained object tag based at least in part upon whether at least four analyzed features satisfy at least four pre-determined properties.

23. The method of claim 16, further comprising the step of removing structured background items from the medical image.

24. The method of claim 16, wherein step (b) further comprises identifying the potential site in the medical image in which the retained object tag may be present based at least in part upon pixel response values of individual pixels in the medical image.

25. The method of claim 16, wherein step (c) further comprises analyzing the feature of the identified potential site against the pre-determined property of the retained object tag via an artificial neural network that outputs a checkpoint value representing a likelihood that the identified potential site is a retained object tag.

26. The method of claim 16, wherein the analyzed feature of step (c) comprises a geometric property of the identified potential site or of the retained object tag.

27. The method of claim 16, wherein step (c) further comprises analyzing the identified potential site against at least two pre-determined properties, and step (d) further comprises determining whether the identified potential site is the retained object tag based on whether the analyzed feature satisfies both of the at least two pre-determined properties.

28. The method of claim 16, wherein step (c) further comprises analyzing the similarity between the identified potential site and the retained object tag, and step (d) further comprises determining whether the identified potential site is the retained object tag based on the analyzed similarity.

29. The method of claim 28, wherein step (c) further comprises analyzing the similarity via at least one pre-determined template created using a plurality of medical images containing the retained object tag at different orientations, using a plurality of objects, or using both.

30. The method of claim 16, wherein step (e) further comprises outputting at least one of: i) a degree of likelihood that the identified potential site is the retained object tag; ii) the location of the retained object tag in the medical image; or iii) the type of retained object in the medical image.

31. A computer readable medium comprising a non-transient data storage device having stored thereon instructions that carry out the method of claim 15.

32. A computer-aided detection system configured to carry out the method of claim 15.

* * * * *